US007694457B2

(12) United States Patent
Martinell et al.

(10) Patent No.: US 7,694,457 B2
(45) Date of Patent: Apr. 13, 2010

(54) METHOD AND APPARATUS FOR PREPARATION OF GENETICALLY TRANSFORMABLE PLANT TISSUE

(75) Inventors: Brian J. Martinell, Mount Horeb, WI (US); Beth Jo Calabotta, University City, MO (US); Richard J. Heinzen, North Freedom, WI (US); Richard F. Klemm, North Freedom, WI (US); Dennis E. McCabe, Middleton, WI (US); Gail A. Roberts, Madison, WI (US); Lori Ann Smith, Lake Mills, WI (US)

(73) Assignee: Monsanto Technology LLC, St. Louis, MO (US)

( * ) Notice: Subject to any disclaimer, the term of this patent is extended or adjusted under 35 U.S.C. 154(b) by 0 days.

(21) Appl. No.: 12/047,212

(22) Filed: Mar. 12, 2008

(65) Prior Publication Data

US 2008/0179435 A1 Jul. 31, 2008

Related U.S. Application Data

(62) Division of application No. 10/710,067, filed on Jun. 16, 2004, now Pat. No. 7,402,734.

(60) Provisional application No. 60/320,278, filed on Jun. 16, 2003.

(51) Int. Cl.

| | |
|---|---|
| ***A01C 1/00*** | (2006.01) |
| ***A01G 7/00*** | (2006.01) |
| ***A01H 4/00*** | (2006.01) |

(52) U.S. Cl. ................................................ 47/58.1 SE

(58) Field of Classification Search ................. 800/278, 800/279, 287; 435/420; 426/483, 622; 47/58.1, 47/57.6, 58.1 SE See application file for complete search history.

(56) References Cited

U.S. PATENT DOCUMENTS

| | | | | |
|---|---|---|---|---|
| 1,849,786 | A | 3/1932 | Bloede et al. | |
| 3,301,292 | A | 1/1967 | O'Connor | |
| 3,744,399 | A * | 7/1973 | Bonteil | 426/483 |
| 4,220,287 | A | 9/1980 | Boczewski | 241/9 |
| 4,986,997 | A | 1/1991 | Posner et al. | 426/622 |
| 5,952,230 | A | 9/1999 | Kim et al. | 435/415 |
| 6,070,815 | A | 6/2000 | Miyatake | 241/47 |

(Continued)

FOREIGN PATENT DOCUMENTS

EP 0 339 577 11/1989

(Continued)

OTHER PUBLICATIONS

Green et al., "Plant regeneration from tissue cultures of maize," *Crop Sci.*, 15:417-421, 1975.

(Continued)

*Primary Examiner*—Kent L Bell
(74) *Attorney, Agent, or Firm*—Thomas P. McBride, Esq.; Sonnenschein Nath & Rosenthal LLP

(57) ABSTRACT

A process of mechanical separation of embryos from seeds for genetic transplantation employs counter-rotating cylinders together with one or more culling, hydration, separation, and viability testing steps to provide high-throughput of viable, transplantable tissue.

26 Claims, 9 Drawing Sheets

U.S. PATENT DOCUMENTS

| | | | | |
|---|---|---|---|---|
| 6,384,301 | B1 | 5/2002 | Martinell et al. | 800/294 |
| 7,150,993 | B2 | 12/2006 | Davis et al. | 800/278 |
| 7,402,734 | B2 | 7/2008 | Martinell et al. | 800/287 |
| 2002/0120961 | A1 | 8/2002 | Ranch et al. | 800/320.1 |
| 2005/0042305 | A1 | 2/2005 | Endo et al. | 424/725 |
| 2005/0246786 | A1 | 11/2005 | Adams et al. | 800/278 |
| 2006/0005273 | A1 | 1/2006 | Rudrabhatia et al. | 800/278 |
| 2008/0179435 | A1 | 7/2008 | Martinell et al. | 800/278 |
| 2008/0182330 | A1 | 7/2008 | Martinell et al. | 435/420 |
| 2009/0029449 | A1 | 1/2009 | Adams et al. | 435/285.1 |

FOREIGN PATENT DOCUMENTS

| | | |
|---|---|---|
| EP | 0 356 987 | 3/1990 |
| GB | 402848 | 12/1933 |
| GB | 861711 | 2/1961 |
| JP | 017107 | 1/2001 |
| JP | 292717 | 10/2001 |
| JP | 2002-119886 A | 4/2002 |

OTHER PUBLICATIONS

Kumlehn et al., "In vivo development of wheat (*Triticum aestivum* L.) from zygote to plant via ovule culture," *Plant Cell Reports*, 16:663-667, 1997.

Laurie et al., "A novel technique for the partial isolation of maize embryo sacs and subsequent regeneration of plants," *In Vitro Cell Dev. Biol.—Plant*, 35:320-325, 1999.

* cited by examiner

METHOD AND APPARATUS FOR PREPARATION OF GENETICALLY TRANSFORMABLE PLANT TISSUE

CROSS REFERENCE TO RELATED APPLICATIONS

This application is a division of U.S. application Ser. No. 10/710,067, filed Jun. 16, 2004 now U.S. Pat. No. 7,402,734 which claims the benefit of U.S. Provisional application 60/320,278 filed Jun. 16, 2003, each of the disclosures of which are hereby incorporated by reference in their entirety.

BACKGROUND OF INVENTION

The present invention relates to plant cell transformation in which genetic material is inserted into plant cells to modify resulting plants, and in particular, the invention relates to an apparatus for collecting embryonic tissue from seeds that may be used for such transformation.

The genetic transformation of plants may be used to develop crops with improved yield, insect and disease resistance, herbicide tolerance, and increased nutritional value. In such transformation, new genes are introduced into the chromosomal material of existing plant cells. Various methods have been developed for transferring genes into plant tissue including high velocity microprojection, microinjection, electroporation, direct DNA uptake and, *Agrobacterium*-mediated gene transformation.

Once the gene is successfully introduced into the chromosomal material of the plant cells, new inheritable germ line tissue must be developed (e.g., seeds) so that the new plant may be propagated. One way this may be done is by selecting only cells that have accepted the new gene and culturing the callus of these cells into a new viable plant. The time required to develop a plant from a single cell is lengthy.

Shortened development times may be obtained by directly treating meristematic tissue of a preformed plant embryo. The meristematic tissue is formative plant tissue of cells that will differentiate to produce different plant structures including the seeds or germ line tissue. A number of plant embryos may be treated and selection or screening techniques used later to determine which of those plants have incorporated the new genetic information into their germ line tissue.

U.S. Pat. No. 6,384,301 assigned to the assignee of the present invention and hereby incorporated by reference describes a method of genetically transforming soybeans (*Glycine max*) using *Agrobacterium* mediated gene transfer directly on the meristematic cells of soybean embryos. In this procedure, the seeds are soaked to initiate germination. After germination has begun, the embryo is excised from the seed and the primary leaf tissue removed to expose the meristem of the soybean embryo. The meristem is formative plant tissue that will differentiate to give rise to different parts of the plant.

Although seeds are inexpensive, the considerable labor involved in excising the embryos, transferring the genetic material into the embryos, and cultivating the embryos makes it desirable to reduce damage to the embryo that could result in this effort being applied to tissue that is ultimately non-viable. For this reason, the excision of plant embryos is performed by hand.

In the manual process, surface sterilized seeds are aseptically handled one at a time with gloved hands. They are oriented in a manner as to eject the seed coat with applied force. Then the cotyledons are separated and removed leaving the seed embryo. The embryonic leaves are removed near the area of the primary meristem. Recovery of viable embryos for genetic transfer is less than 100% even with this hand method and may be as little as 70% with high quality seeds.

Bacterial contamination of the embryos after excision is a significant concern. Manual excision of the embryos allows early separation of the seed coat from the remainder of the seed to prevent contamination of the embryo with bacteria found on the seed coat, which normally protects the embryo.

Skilled personnel performing manual excision can often recognize abnormal embryos at the time of excision and discard them, substantially improving downstream yields.

Despite the advantages of manual excision, individual separation of each plant embryo from its seed is extremely labor intensive and stands as a barrier to a scaling up of the transformation process in which, typically, many plants must be treated to yield a successful few transformations.

What is needed is a process that can significantly increase the availability of transformable embryos without unacceptably increasing total costs of transformation, the latter which will rise if damage to embryos or bacterial contamination of the embryos causes fruitless cultivation of large numbers of non-viable embryos.

SUMMARY OF INVENTION

The present inventors have developed an automated technique for excision of transformable tissue from seeds that sufficiently reduces embryo damage and bacterial contamination such as might render mechanical separation impractical. A mechanical excision machine is combined with optional seed culling, improved hydration of the seeds, and automated separation of the embryos to make automatic excision practical. Additional techniques to reduce bacterial contamination incident to such automation, particularly between the seed coat and the embryo, are provided.

Specifically then, the present invention provides for automated preparation of transformable plant tissue by hydrating plant seeds to soften the seed tissue and then passing the hydrated seeds through a mechanical separator that divides the seeds into separate cotyledon, seed coat and embryo. Genetic material is then introduced into the cells of the separated embryo.

It is one object of the invention to provide for the high volume automated excision of transformable plant tissue.

The mechanical separator may provide opposed moving surfaces applying a shear force to the hydrated seeds.

It is another object of the invention to provide for a simple mechanical separator that separates the seed components without undue damage to the embryo. The shear force on the hydrated seeds coaxes the seeds apart along their natural separation points.

The opposed moving surfaces may be rollers having different rolling speeds.

Thus it is another object of the invention provide for shear surfaces that are easily manufactured.

The rollers may be co-rotating.

It is another object of the invention to provide a mechanism that is adaptable to a continuous or semicontinuous batch process.

The rollers may have serpentine roller faces.

It is another object of the invention to provide a surface that envelops the outer surface of the seeds to separate them and distribute the shearing force evenly to reduce damage to the embryos.

The rollers may have an outer elastomeric surface.

Thus, it is another object of the invention to provide for improved grip and reduced pressure on the seed coat.

The moving surfaces may comprise at least two successive sets of opposed rollers.

Thus, it is another object of the invention to provide for a series of graduated separations of the seed coats to increase yield.

The separation of the moving surfaces may be adjusted according to the type of seeds. The amount of shear between the moving surfaces may also be adjusted according to the type of seed.

Thus, it is another object of the invention to provide a machine suitable for the processing of a variety of different seed types.

The seeds may be sprayed with liquid as they pass through the mechanical separator.

It is another object of the invention to reduce bacterial contamination incident to such mechanical separations by a constant dilution or disinfecting of such contamination with sterile liquid or a disinfectant solution.

Liquid may be sprayed against the rollers to strike the rollers in a direction opposite rotation of the rollers.

It is another object of the invention to provide for a cleaning of the rollers that minimizes damage to attached embryos.

The volume or mass flow of seeds into the mechanical separator may be controlled to a predetermined constant value.

It is thus another object of the invention to minimize damage to the embryos that may be caused by an excessive number of seeds entering the rollers.

The seeds may be culled based on predetermined seed characteristics such as color, size, moisture, germplasm or density prior to their mechanical separation.

Thus it is another object of the invention to compensate for the lack of human visual inspection in mechanical excision by a tight control of seed type at a stage where rejection of seeds is relatively inexpensive.

The step of hydrating the seeds may include rinsing the seeds and then holding them for at least one hour followed by a soaking of the seeds.

It is thus another object of the invention to provide for a hydration in a manner that reduces cracking of the cotyledons such as may promote damage to the embryo.

The rinsing, holding, and soaking may be performed in a container in which seeds are introduced, the container having a drain and an inlet, the inlet communicating with the first rinse liquid reservoir, and a second soak liquid reservoir different from the rinse liquid reservoir and including a valve position between the inlet and the rinse liquid reservoir and the inlet and the soak liquid reservoir and the drain, the valve communicating with an electronic timer for controlling the rinse, holding, and soaking automatically.

Thus it is another object of the invention to allow more complex schedules for hydrating the seeds without undue seed handling. It is another object of the invention to allow the use of reservoirs into which different additives may be introduced permitting different rinse and soak materials to be used in hydrating the seeds.

The rinse may include an antimicrobial such as a bleach or other disinfecting solution.

Thus it is another object of the invention to reduce the bacterial load upstream of their mechanical excision, the latter which may cause contamination of the embryos.

After the mechanical separation, the cotyledons, seed coats, and embryos may be passed into a separating machine to separate the embryos from the seed coats and the cotyledons.

Thus it is another object of the invention to eliminate the need to manually sort through separated seed material such as would reduce the benefit of mechanical excision.

The separating machine may include a weir allowing the seed coats to wash over the top of the weir and the embryos and cotyledons to pass to the bottom of the weir.

Thus it is another object of the invention to provide a separation system that works naturally with the mixture of liquid and seed parts exiting the separation machine. It is another object of the invention to separate the dirty seed coats from the embryos early in the separation process to reduce the risk of contamination.

The separating machine may include a screen separating the cotyledons from the embryos.

Thus it is another object of the invention to reduce manual effort necessary to extract the embryos from the cotyledons.

The method may include, after the mechanical separation, a step of culturing the embryos for a predetermined period in a liquid medium to cull nonviable embryos.

It is thus another object of the invention to provide a mechanism that may, if necessary, accommodate a higher rate of nonviable embryos in mechanical separation without incurring excessive cultivation costs.

These particular objects and advantages may apply to only some embodiments falling within the claims and thus do not define the scope of the invention.

DETAILED DESCRIPTION

Figure 1:
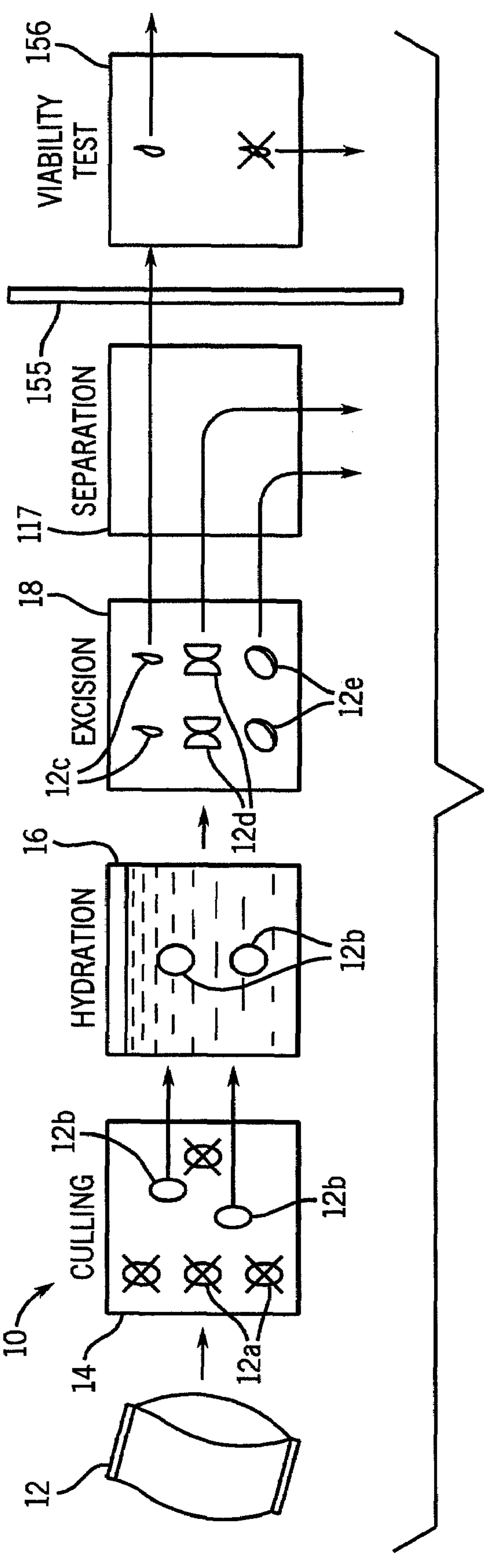
FIG. 1 is a flow chart showing principal steps of the present invention such as may include: culling, hydration, excision, separation, and a viability test.

Referring now to FIG. 1, generally the mechanized method 10 of the present invention receives harvested soybeans or other seeds 12 from which transformable plant tissue will be extracted. The seeds 12 are ideally harvested at a predetermined internal moisture suitable for isolating transformable material therefrom, e.g., 8-14% internal moisture for soybeans, and held in stable storage conditions prior to use.

The seeds 12 may be subject to an optional culling step 14 intended to remove seeds 12*a* with a high degree of bacterial or fungal contamination and also seeds 12*a* that may for any reason statistically fail to produce viable embryonic tissue with the present invention. These latter reasons may include parameters such as the size of the seed or other physical characteristics that in other contexts would be unobjectionable and may be adjusted empirically by variation of the parameters and measurement of ultimate yields of the viable tissue.

Preferably, the culling step 14 is performed mechanically and may include a size culling using standard seed sorting techniques eliminating the seeds 12 above and below a predetermined size, optical sorting using high speed sorting equipment readily available on the market such as employs a camera and vision system to reject seeds 12 that are selected from one or more of the following criteria, color, size, shape or density. Examples of culling methods may include the use of an automatic scale after size sorting, or an optical sorter suitable for this purpose is the Satake Scan Master II manufactured by Satake USA Inc., of Houston, Tex. Other culling techniques may also be employed including culling by moisture content. Culling may also occur after hydration, as it has been determined that seeds with seed coats that have been damaged become imbibed faster than seeds with intact seed coats.

The culling step 14 is intended in part to replace the unconscious selecting of seeds by technicians performing the manual excision of the prior art, and to reduce bacterial and fungal load on the seeds 12 that may, in the mechanical process, create greater potential for contamination of the embryos. The optional culling step 14 may be quite aggressive because the seeds 12 prior to the excision are inexpensive.

Figure 2:
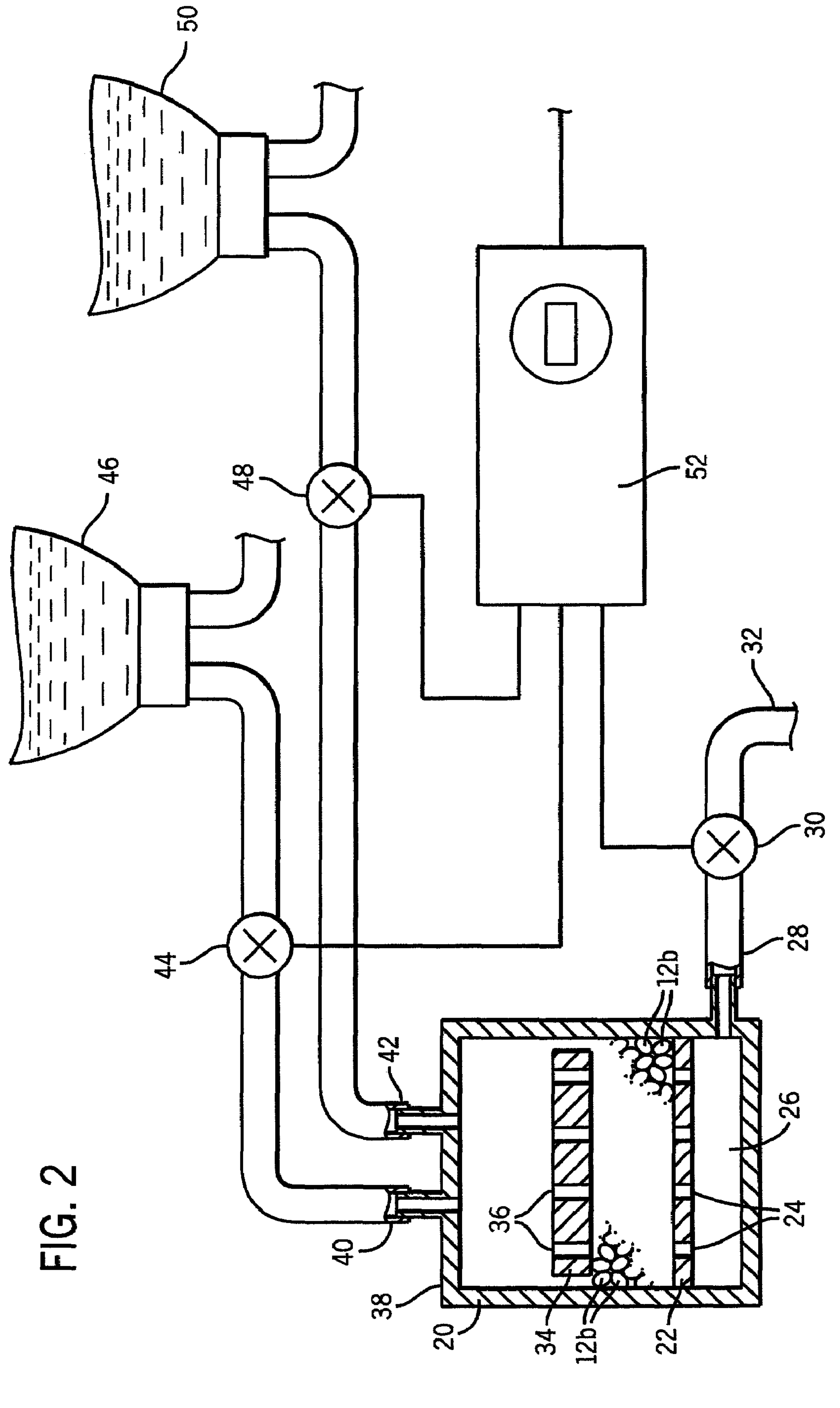
FIG. 2 is a schematic diagram of an apparatus used in the hydration step of FIG. 1 allowing automatic control of seed hydration.

Referring now to FIG. 2, the seeds 12*b* that pass the optional culling step 14 move to an optional hydration step 16 in which liquid may be introduced into the seeds 12 to soften the cotyledons and the seed coats reducing the possibility of damage of the embryo during the following excision step 18. The hydration step 16 is preferably performed automatically, but may be performed manually. Referring again to FIG. 2, in a preferred embodiment hydration is performed through the use of a sterilized hydration container 20 having a four-liter capacity and a false bottom 22 perforated by a series of holes 24 smaller than the size of the seeds 12*b*. The holes 24 lead to a drain chamber 26 communicating via an outlet hose 28 and valve 30 to a drain 32.

The seeds 12 are placed on top of the false bottom 22 and a retainer plate 34 having holes 36, also smaller than the average seed 12*b*, is placed to rest lightly on top of the seeds 12*b* to prevent them from floating. An upper, removable lid 38 of the container 20 provides two inlets 40 and 42. The first inlet 40 communicates via valve 44 to a rinse reservoir 46 containing a solution of sterile liquid and 200 ppm of Clorox. The second inlet 42 communicates via valve 48 to a tissue culture solution reservoir 50 containing a suitable plant tissue culture medium, such as bean germination medium (BGM) as described in U.S. Pat. No. 6,384,301. The tissue culture medium may also contain antimicrobials such as cefotaxime, Bravo, Benlate, Captan, and Carbenicillin. Other fungicides, disinfectants, plant hormones, antibiotics, and hydrogen peroxide may optionally be used in the tissue culture solution reservoir 50. The liquid in both reservoirs 46 and 50 is held at room temperature.

An electronic timer 52 communicates with each of the valves 44, 30, and 48 and is programmed so to initially, at a predetermined time before the excision process, to close valve 30 and open valve 44 for a predetermined time to fill the container 20 with the rinse solution from the rinse reservoir 46 after which valve 44 is closed. The rinse solution is held in place for three to ten minutes as valve 30 is opened to drain the container 20 through outlet hose 28.

This first rinsing of the seeds 12*b* allows them to begin to absorb moisture but is not so pronounced as to cause cracking of the cotyledons such as might be caused by uneven expansion of the cotyledon material in the presence of excessive liquid. Rinsing also serves to further reduce surface contaminants. Other ways to prevent cracking include pre-incubation in a humid atmosphere or seed priming.

At least one hour later and preferably two hours later, the timer 52 operates to close valve 30 and open valve 48 for a predetermined time to fill the container 20 with the tissue culture media from the tissue culture solution reservoir 50. The tissue culture media is held within the chamber for 8-13 hours after which the tissue culture media is drained by the timer 52 opening valve 30. The container 20 is then refilled (via valve 44 operated by timer 52) with rinse solution from the rinse reservoir 46 for 15-30 minutes without draining (timer 52 holding valve 30 closed), the excess solution being used as a carrier for the excision step or drained (i.e., for use with an auger) as will now be described. When the seeds 12 are contained in a tissue culture medium without circulation, an ethylene inhibitor may be used.

Other methods of hydration are also contemplated in the present invention including an aerobic method in which the liquid is sprayed on the seeds without accumulating or where a gas is bubbled through the growth medium using an aerator or the like or media may be recirculated. It is also envisioned that other sizes and shapes of containers with different combinations of inlets and outlets, different methods of separating liquid from seeds, different solutions for different times, and the like may also serve the purpose of hydration.

Figure 3:
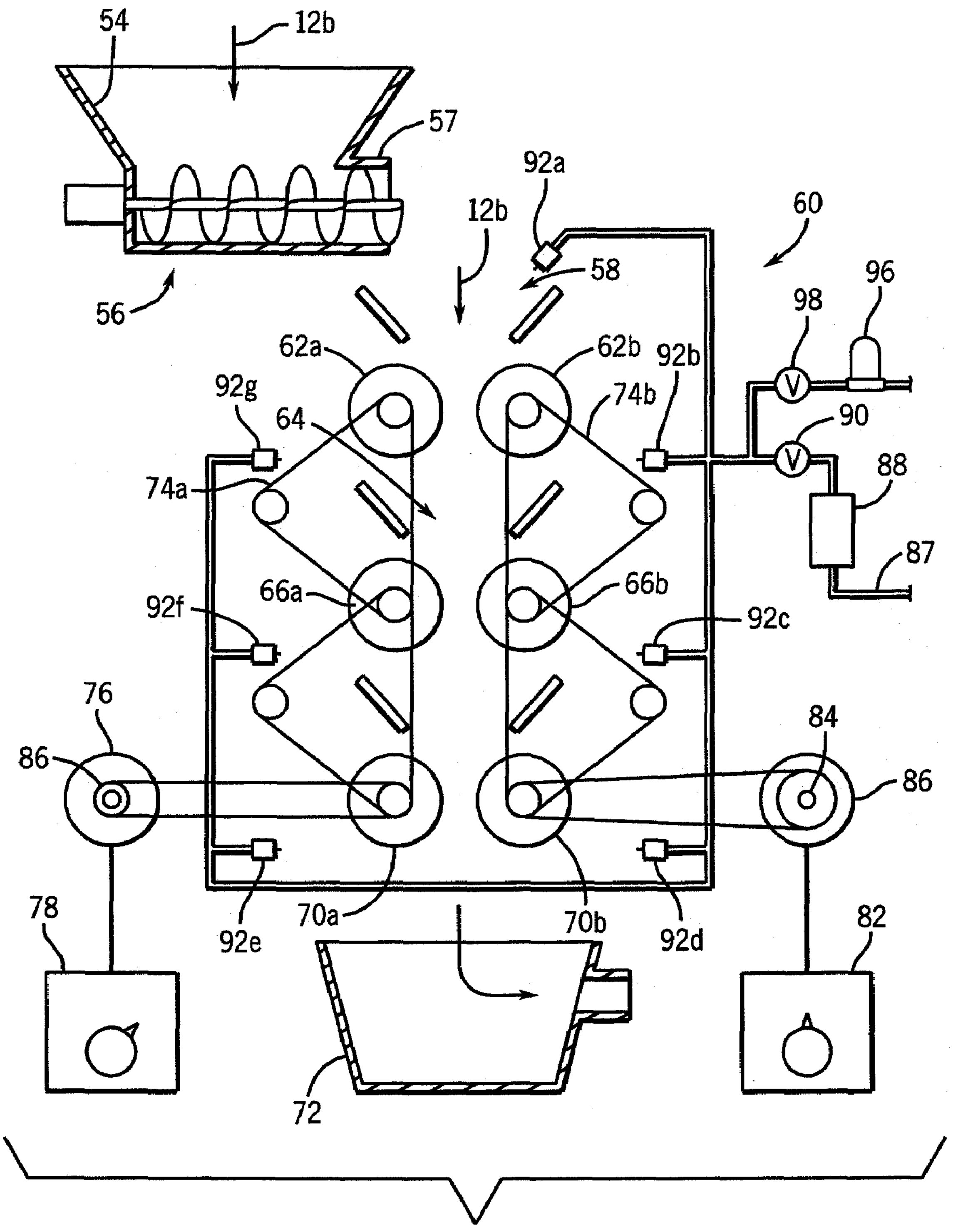
FIG. 3 is a simplified representation of an apparatus used in the excision step of FIG. 1 providing a series of opposed rollers which separate the seed parts by a sheering action.

Referring now to FIGS. 1 and 3, after hydration, the seeds 12*b* are poured together with the rinse liquid into a hopper 54 of an auger feed 56 such as provides a controlled feeding of the seeds 12*b* and rinse liquid into a first hopper 58 of an automated excision machine 60. Such auger feeds 56 are well known in the art. The speed of the feeding of the seeds 12*b* is determined initially by inspection to reduce clumping of the seeds 12*b* at the rollers and to minimize visual damage to the embryos. Ultimately this feed speed may be determined empirically by using varying speeds and observing embryo viability. The auger feed 56 may be an Accu-Rate Feeder, manufactured in Whitewater, Wis. Other feed systems may be used in place of the auger feed 56 including, for example, pumps (with the seeds held in a slurry), conveyor belts, or vibrating conveyor systems such as are well known in the art. In addition, the rinse liquid could be separated from the seeds prior to input into the feeder. This step may also be performed manually without the use of a feeder.

Figure 13A:
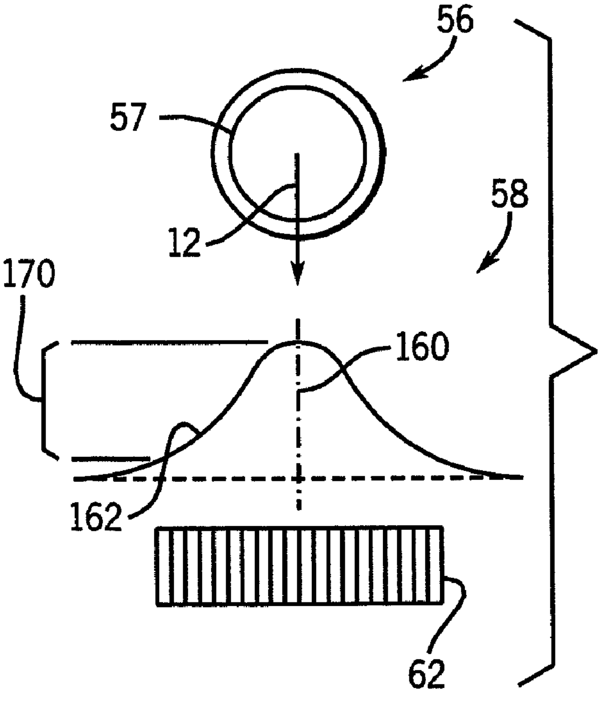
FIGS. 13*a* and 13*b* are simplified elevational views of the path of seeds from an auger feeder into the apparatus of FIG. 3, the elevational views superimposed on plots of seed distribution with and without a spreader bar used to provide a more uniform seed distribution.

Referring now to FIGS. 3 and 13*a*, the auger feed 56 provides a discharge tube 57, ejecting seeds 12 along a horizontal axis perpendicular to the axis of rotation of rollers 62, 66 and 70 as will be described below. The seeds 12 fall from the discharge tube 57 through hopper 58 into a gap between the rollers 62, concentrated along a centerline 160 by the limited size and circular aperture of the discharge tube 57.

This spatial concentration of seeds 12, shown by a seed distribution curve 162 peaking near the centerline 160, can cause a crushing of seeds 12 when multiple seeds 12 pass through the rollers 62 gapped to provide efficient separation of the seed coat embryos and cotyledons at the edges of the rollers 62.

Figure 13B:
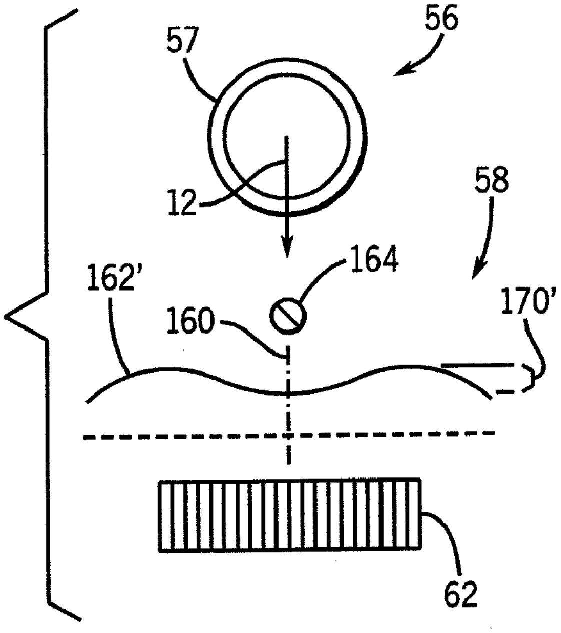

Accordingly, referring to FIG. 13*b*, a diverter bar 164 may be placed between the discharge tube 57 and the rollers 62 extending fully across the hopper 58 along the axis of discharge tube 57 at the centerline 160. This diverter bar 164 reduces the peak of the new seed distribution 162' providing a smaller seed distribution variance 170 than the seed distribution variance 170' obtained without the diverter bar as shown in FIG. 13*a*.

Similar methods of mechanical redistribution to even the solid flows may be made prior to or between successive sets of rollers if more than one roller pair are utilized.

The rollers 62, 66 and 70 are part of an automated excision machine 60 performing the excision step 18 of the present invention to separate the seeds 12*b* into embryos 12*c*, cotyledons 12*d*, and seed coats 12*e*. The excision operation may be conducted in a clean room to minimize contamination from bacteria and mold.

The first hopper 58 of the automated excision machine 60 directs the seeds 12*b* into a pair of horizontally opposed rollers 62, each rotating about mutually parallel horizontal axes. The seeds 12 pass through these rollers 62 to be received by a second hopper 64 and a second pair of horizontally opposed rollers 66 with mutually parallel horizontal axes. The seeds 12 pass between these rollers 66 and are received by a third hopper 68 and a following third pair of horizontally opposed rollers 70 with mutually parallel horizontal axes.

From the last set of rollers 70, the seeds 12 fall into a collection vessel 72 as will be described further below. The use of three separate stages of rollers ensures that the components of most seeds 12 are fully separated by the time they arrive in the collection vessel 72.

The left rollers as depicted in FIG. 3, (i.e., rollers 62*a*, 66*a* and 70*a*) turn clockwise in unison as driven by overlapping timing belts 74*a* which is driven by a first motor 76 attached to a first motor controller 78. The clockwise direction causes a downward progression of the seeds 12 between the roller pairs.

Similarly, the right rollers as depicted in FIG. 3, (i.e., rollers 62*b*, 66*b* and 70*b*) are interconnected by overlapping timing belts 74*b* and turned by a second motor 80 having an independent second motor controller 82. Here, a counterclockwise direction causes a downward progression of the seeds 12 between the roller pairs.

A sprocket 84 on motor 80 and engaging with the teeth of the timing belt 74 is larger than the corresponding sprocket 86 on motor 76 so as to provide a different (faster) rotational rate to the rollers 62*b*, 66*b*, and 70*b* on the right than the rollers 62*a*, 66*a*, and 70*a* on the left. For example, the rollers on the right may turn at about 30 rpm and the rollers on the left may turn at about 90 rpm. The motor controllers 82 and 78 may be adjusted to further refine the speed difference. Seeds 12 contacting both rollers of a pair thus experience a shear force acting on their outer surfaces.

It will be understood that other methods of driving the rollers at controlled speeds may be used including gear drives, direct drive servo motors, and the like. It is also understood that different speeds of turning the rollers may be used.

Referring still to FIG. 3, a sterile liquid or disinfectant solution source may attach through liquid line 87 to a flow meter 88 to be metered via pressure regulator 90 into a manifold connected to a set of spray heads 92*a* through 92*g*. The liquid may further contain additional ingredients to surface sterilize or condition the embryos including but not limited to disinfectants, ethylene inhibitors, antioxidants, and surfactants. Spray head 92*a* is directed down-ward through hopper 58 to provide a steady wash of sterile liquid or disinfectant solution to wash the seeds 12 through the excision machine 60 and to lubricate and orient the seeds 12 and to dilute any contamination that may be introduced from the seed coats 12*e*. The rate of liquid flow and pressure may be controlled to empirically determined values.

Spray heads 92*e* through 92*g* spray the under surface of rollers 70*a*, 66*a*, and 62*a*, respectively, directed against the tangential direction of rotation of the rollers to help dislodge seed material stuck on the rollers and further urge the seed through the machine. Likewise, spray nozzles 92*c* through 92*f* spray the under surface of rollers 62*b*, 66*b*, and 70*b*, respectively, directed against the tangential direction of rotation of the rollers.

It is anticipated that other methods may be used to introduce liquids into this step. Examples include, but are not limited to, the use of a distribution manifold, overflow weir, pipe, etc.

A sterile air source from air filter 96 may be connected to the liquid manifold via a valve 98 to purge the water lines between use to prevent the accumulation of biofilm and bacterial contamination. The air further dries the lines and provides a positive pressure to the lines reducing the risk of contamination of the lines.

Figure 4:
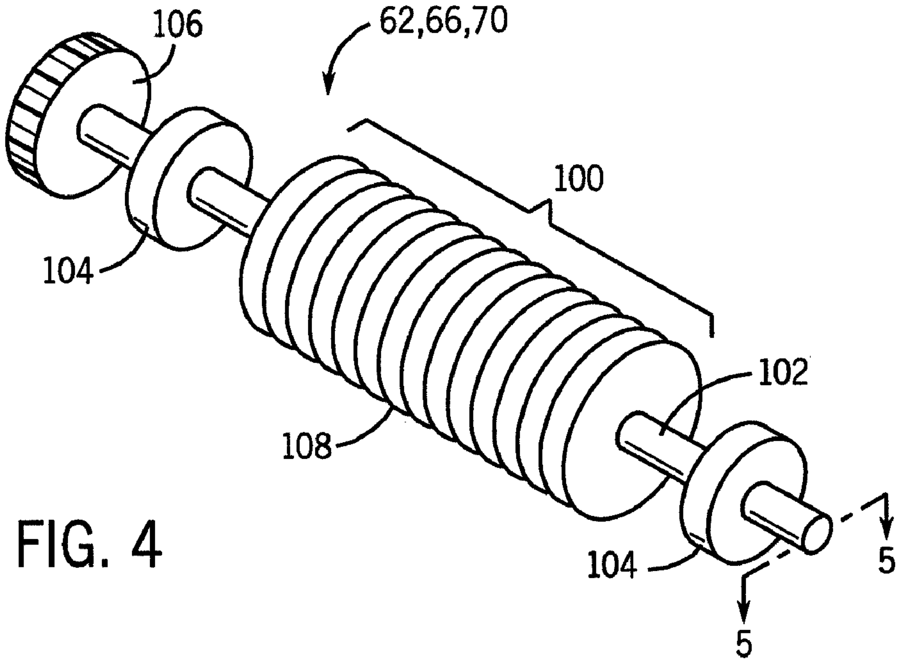
FIG. 4 is a perspective view of one roller of the device on FIG. 3.

Referring now to FIG. 4, each roller 62, 66, and 70 has a generally cylindrical central portion 100 presenting a serpentine longitudinal profile 108. The cylindrical central portion 100 is mounted on a concentric longitudinal axle 102. The axle 102 may be supported at either end by conventional ball bearings 104, and includes at one end, a sprocket 106 such as receives toothed timing belts 74*a* or 74*b* as described with respect to FIG. 3. The cylindrical central portion 100 may be coated with an elastomeric material, such as neoprene, Buna-N, chlorobutyl, EPDM, Viton, etc., that is resistant to wear and provides a cleanable and sanitizable surface that nevertheless is soft so as to conform slightly to the seed 12*b* and to provide improved gripping of the seeds 12. Referring momentarily to FIG. 3, the softness of the elastomeric material may be increased for lower roller pairs with the roller pair 62*a* and 62*b* providing the hardest outer surface and the roller pair 70*a* and 70*b* providing the softest outer surface. For example, the elastomeric material of the upper rollers may be durometer 35 of the next pair of rollers, durometer 25 and 35, and the bottom pair, both durometer 25. It is understood that different seeds may require a particular gap angle, geometry, configuration, outer profile, diameter, or durometer.

Figure 5:
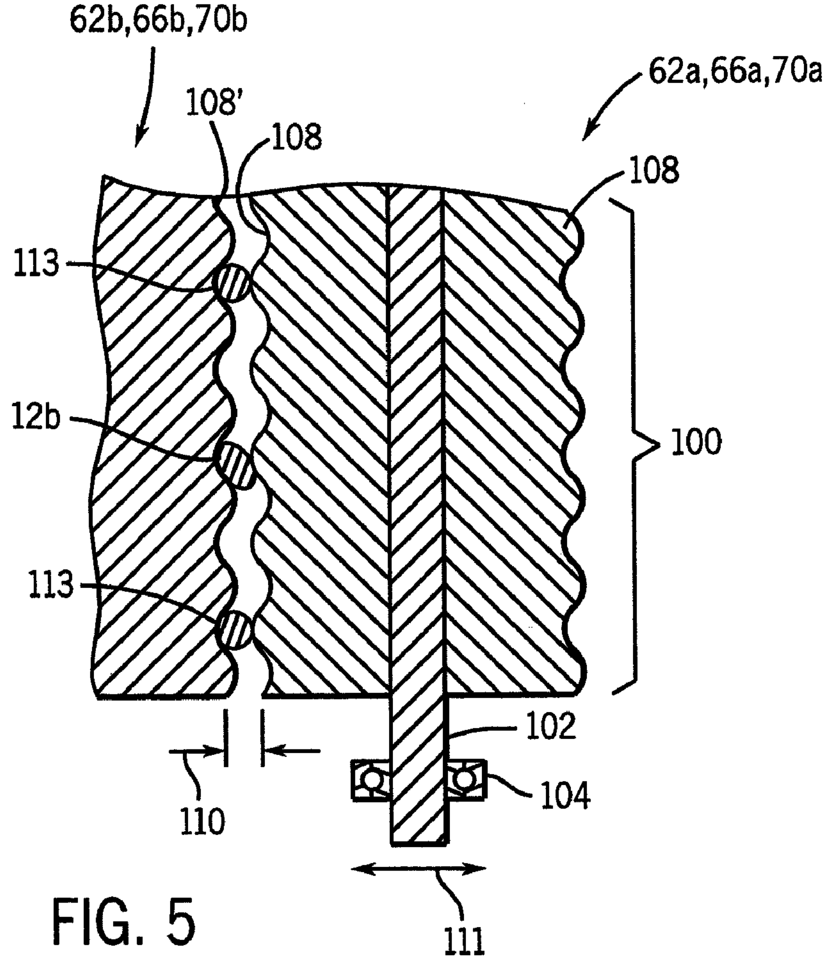
FIG. 5 is a cross-section through a pair of rollers of FIG. 3 taken along line 5-5 of FIG. 4 showing a setting of the separation of the rollers using a gauge.

Referring now to FIG. 5, the serpentine profile 108 of each roller 62*a*, 66*a*, or 70*a* may be aligned with a corresponding surface serpentine profile 108" of the corresponding roller 66*b*, 62*b*, and 70*b* to which it is opposed to create therebetween, a substantially constant width serpentine channel 110 whose cross-section encourages separation of the seeds 12*b* as they pass through the rollers and provides for multiple engaging surfaces that are curved to conform with the curved outer periphery of the seeds 12*b*. Setting of the separation between pairs of the rollers may be accomplished by lateral movement 111 of bearing 104 and may be facilitated by the insertion of a feeler gauge 113 at either edge of the central portion to ensure the rollers are substantially parallel.

Figure 6:
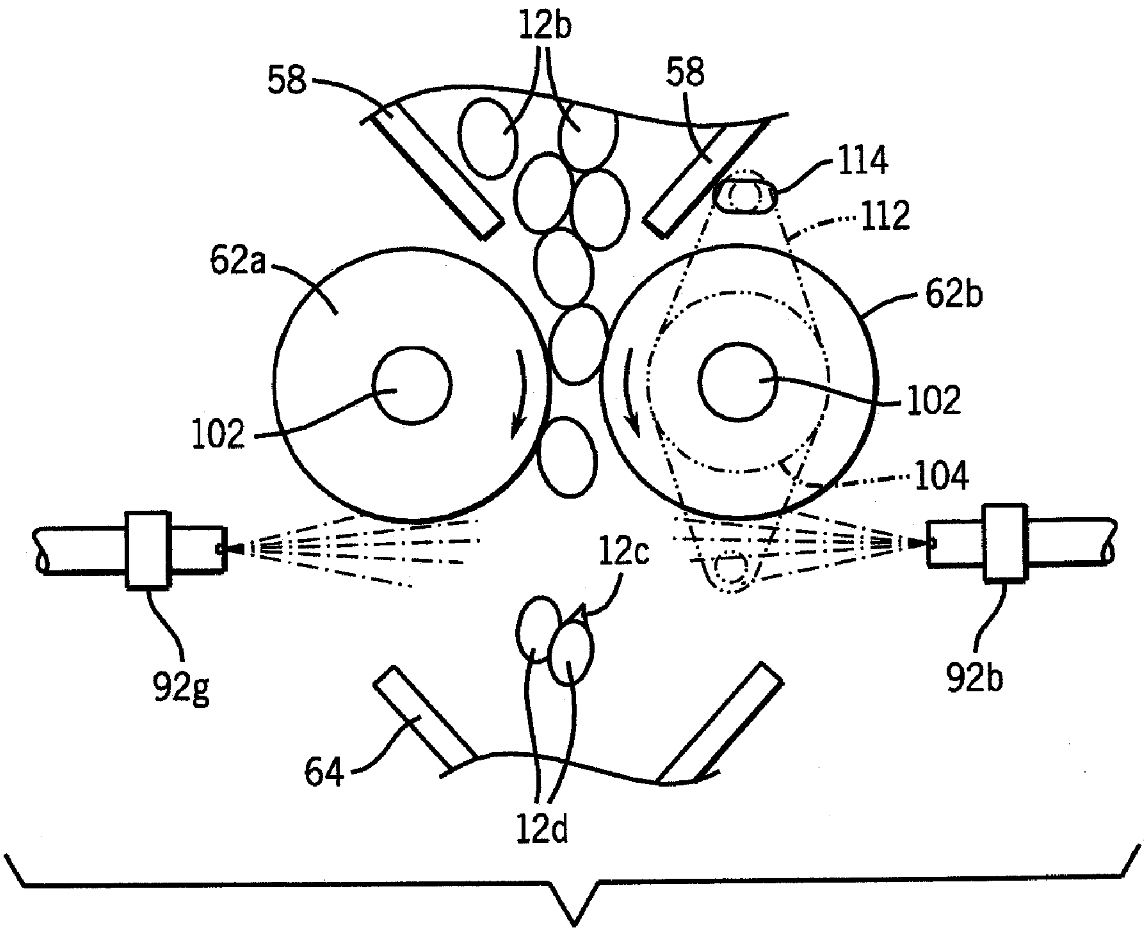
FIG. 6 is a fragmentary enlarged view of one pair of opposed rollers of FIG. 3 showing liquid sprays directed to prevent the rollers from clogging and to direct process flow.

Referring to FIG. 6, the bearing 104 may be held on a pillow block 112 having ears, one of which is mounted pivotally to a frame (not shown) of the automated excision machine 60 and the other which is mounted to an elongated hole 114 in the frame so as to allow lateral motion 111, as shown in FIG. 5. The roller separation or diameter may be changed to accommodate different types of seeds 12 and may be increased for lower roller pairs with the roller pair 62*a* and 62*b* providing the narrowest serpentine channel 110 and the roller pair 70*a* and 70*b* providing the widest serpentine channel.

Other methods of excising the seeds 12 other than rollers are contemplated including disks, rollers with pins and the like which may stab at the cotyledons and press them together.

Figure 7:
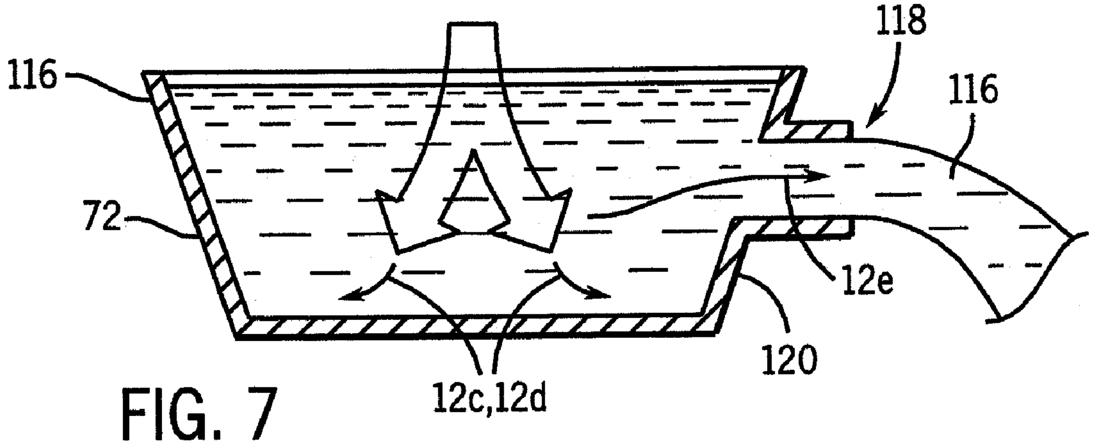
FIG. 7 is an elevational cross-sectional view of a weir in a collection vessel after the final rollers of FIG. 3 such as separates the seed coats from the cotyledons and embryos.

Referring now to FIG. 7, in an initial stage of the separation process 117 (of FIG. 1), collection vessel 72 fills with clean liquid or disinfectant solution 116 produced from the nozzles 92 and also, in part, from the rinse liquid used during the hydration step 16. An opening 118 near the upper edge of the collection vessel 72 provides a weir 120 over which liquid 116 may flow near the surface of the collection vessel 72. Although the inventors do not wish to be bound by a particular theory, it is believed that the seed coats 12*e* entrap air during the excision step 18 and thus float out over the weir 120 to be separated from the cotyledons 12*d* and embryos 12*c*, the latter which settle to the bottom of the collection vessel 72. This early separation of the seed coats 12*e* in a wash of sterile liquid or disinfectant is believed to significantly reduce bacterial or fungal contamination of the embryos 12*c* and prevents the seed coats 12*e* from trapping embryos 12*c* or clogging separation screens in later separation steps.

Figure 8:
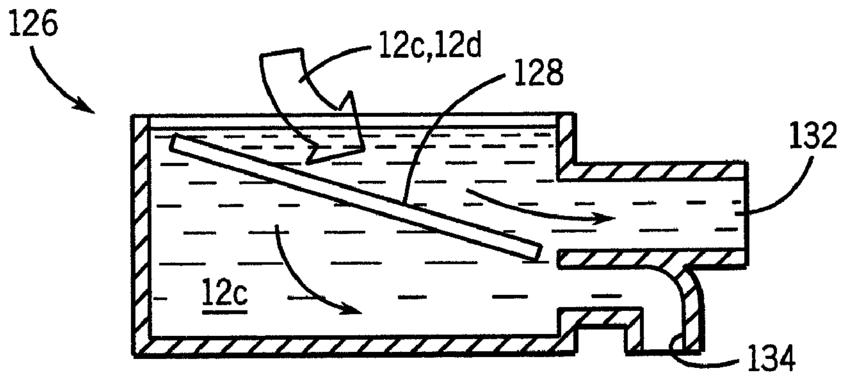
FIG. 8 is an elevational cross-section through a separation device that may follow the weir of FIG. 7 employing a screen to separate the cotyledons and remaining seed coats from the embryos.

Referring now to FIG. 8, the embryos 12*c* may be separated from the cotyledons 12*d* by means of a hydroscreen 126 providing a sloped wire mesh 128 (Tyler number six screen) having square openings approximately one-quarter inch on a side. Other functionally similar materials may be used in place of the wire mesh including, for example, perforated sheets of metal or plastic, loosely woven and non woven fabrics, nets, grids, and the like.

The wire mesh 128 is sloped so that a mixture of cotyledons 12*d* and embryos 12*c* in a sterile liquid or disinfectant solution may be introduced at the upper edge of the sloped wire mesh 128 to wash generally down the slope, at which point embryos 12*c* pass through the wire mesh 128, whereas cotyledons 12*d* follow the wire mesh 128 to its edge and are discharged through an ejection port 132. A separate drain port 134 may be provided for the embryos 12*c*.

Figure 9:
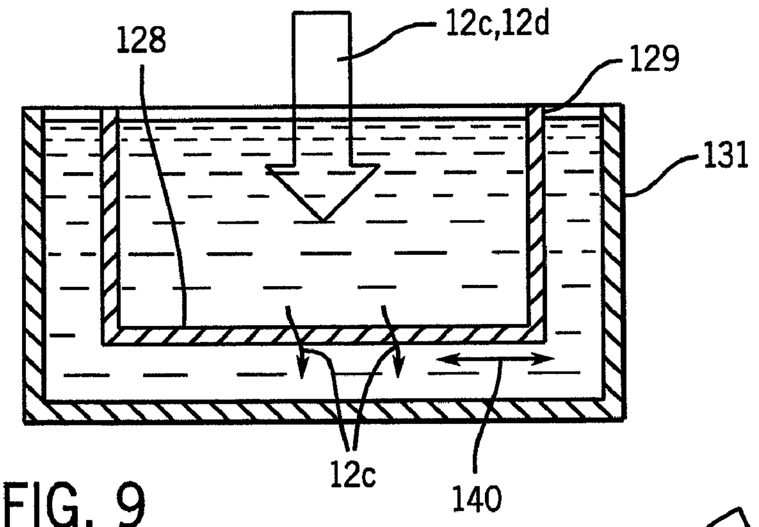
FIG. 9 is a figure similar to FIG. 8 of an alternative embodiment of the separation device using a reciprocating sifting platform.

In an alternative embodiment, the cotyledons 12*d* and embryos 12*c*, as shown in FIG. 9, may be introduced into a tray submerged in sterile liquid or disinfectant solution and having a bottom wire mesh 128. The tray may be reciprocated in a horizontal direction 140 so that the embryos 12*c* pass through the wire mesh 128 into an outer container. The tray 129 may be removed from the outer container 131 and the embryos 12*c* recovered.

Figure 14:
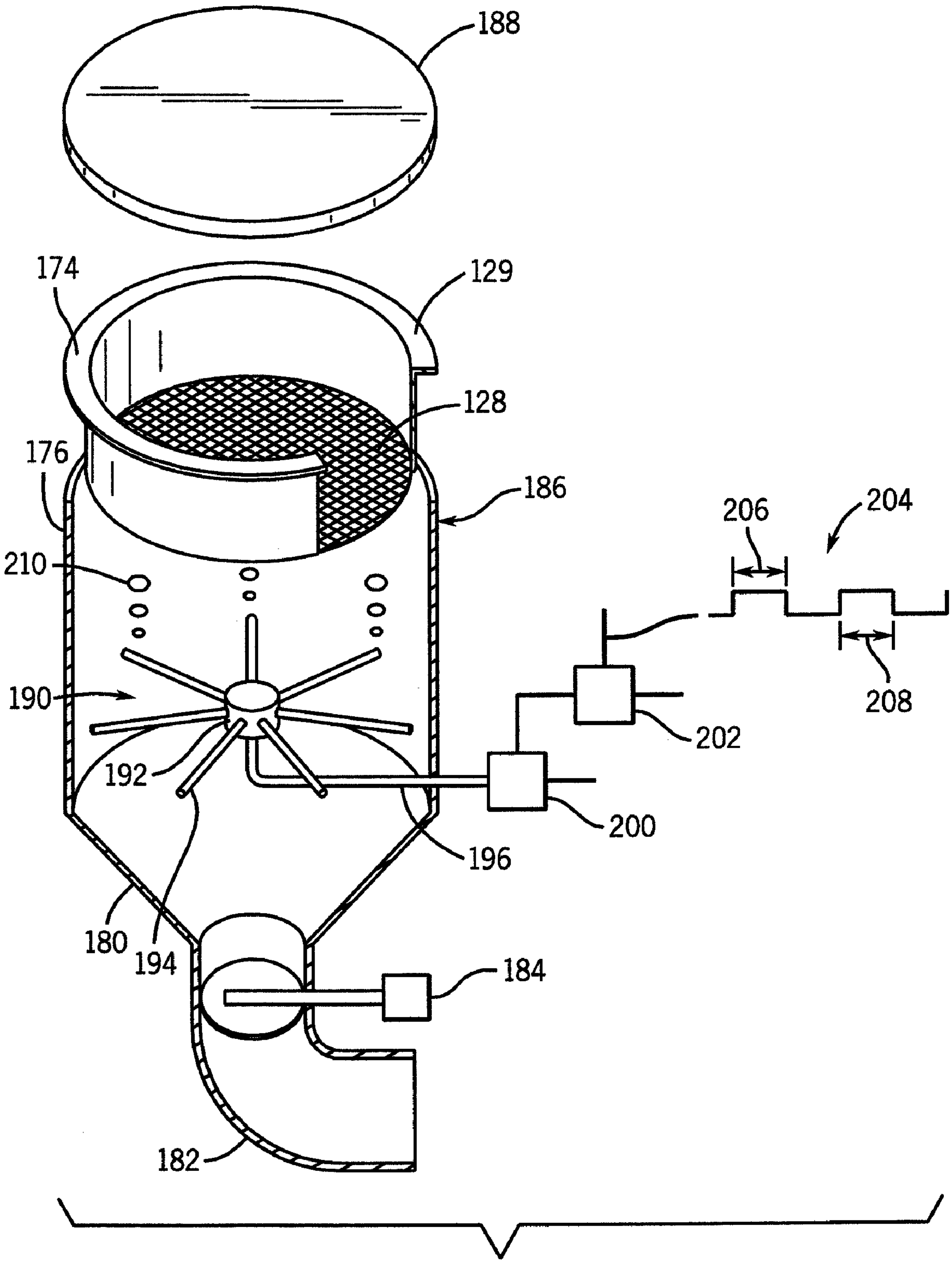
FIG. 14 is an alternative embodiment of the separation devices of FIGS. 8-10 using air agitation.

Referring now to FIG. 14, in an alternative embodiment, the tray 129 of FIG. 9 may be adapted to provide a cylindrical wall with an upper flange 174 allowing it to rest on top of the upper lip of a cylindrical tank 176. As before, the bottom of the tray is fit with a wire mesh 128. The wire mesh 128 is sized to block cotyledons and seed coats but to allow passage of the embryos.

The cylindrical tank 176 is filled with liquid to a liquid level 186 so that seeds placed within the tray 129 (when the tray 129 is in the tank 176) are submerged within the liquid at rest on the wire mesh 128. A cap 188 may fit over the top of the tank 176 covering the tray 129 to pre-vent splashing.

Positioned beneath the tray 129, when the tray is in position in the tank 176, is an aerator assembly 190 having a central hub 192 from which horizontal and radially extending spokes 194 are attached. The hub 192 provides a connection to an air line 196 which receives a source of high-pressure air through valve 200 controlled by pulse timer 202.

Figure 16:
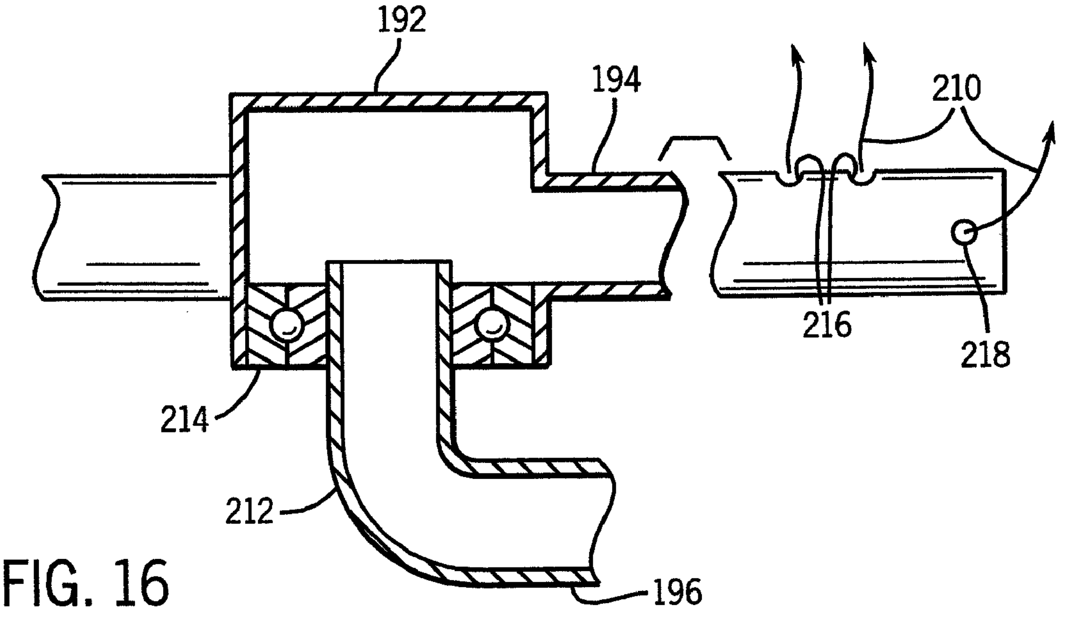
FIG. 16 is a second embodiment of a nozzle assembly for the air agitation of the device of FIG. 14.

Referring to FIG. 16, the hub 192 may be a generally cylindrical inverted cup attached and sealed to a vertical air pipe 212 by a lower bearing 214 fit about the vertical air pipe 212. The bearing 214 allows the hub 192 to rotate freely about a vertical axis. The spokes 194 attached to the hub are hollow tubes communicating with the interior of the hub 192 (and hence with the vertical air pipe 212) at one end and plugged at their opposite ends. The spokes 194 have a series of upwardly facing holes 216 allowing the escape of air bubbles 210 and at least one laterally opening hole 218. This laterally opening hole 218 reinforced by other similarly oriented holes in other spokes 194 provides for rotative motion under the reactive force of escaping air bubbles 210 moving the spokes 194 in a circular motion to ensure even distribution of the air impinging on the bottom of the wire mesh 128.

The pulse timer 202 receives a waveform 204 providing for an agitation time period 206 and a rest time period 208. This duration of each of these time periods 206 and 208 may be freely adjusted so as to provide alternating periods of intense agitation of the liquid in the tray 129 as moved by the liquid roiled by the discharge of air bubbles 210 from the aerator assembly 190.

The discharge of air during the agitation time period 206 is such as to lift the cotyledons, seed coats, and embryos (not shown in FIG. 14) from the wire mesh 128. During the rest time period 208, the lifted material descends again through the liquid so that the embryos may pass through the wire mesh 128 unobstructed by seed coats and cotyledons which tend to fall through the liquid at a different rate.

The tank 176 has a funnel shaped bottom 180 terminating in an outlet for 182 having a control valve 184. The embryos selectively passing through the wire mesh 128 are received by the funnel shaped bottom 180 and may be discharged through the outlet for 182 as controlled by valve 184.

Figure 15:
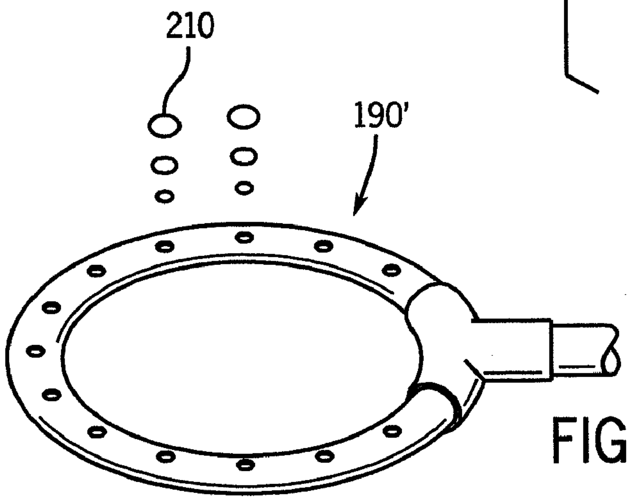
FIG. 15 is a first embodiment of a nozzle assembly for the air agitation of the device of FIG. 14.

Referring to FIG. 15, the air jet assembly 190' may alternatively be a stationary ring or other figuration so as to introduce air bubbles 210 of sufficient volume to provide the necessary agitation. Instead of bubbles, the liquid itself may be pumped using impellers or other pumping systems in place of the air jet assembly 190'.

Sufficient air to produce a vigorous boiling of the liquids within the tray 129 can provide not only improved separation of the seed coats, cotyledons and embryos, but may provide for some excision as well.

Figure 10:
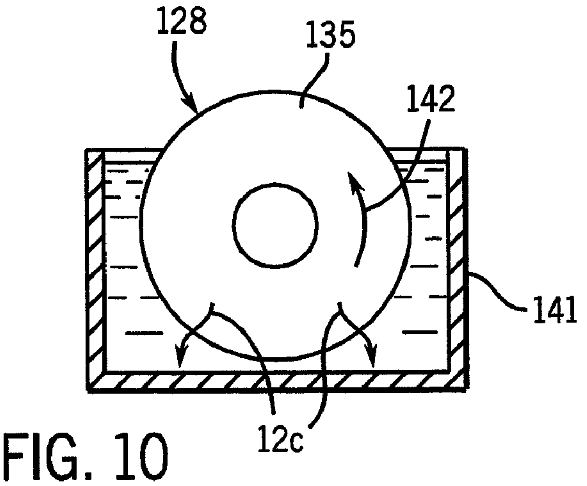
FIG. 10 is a figure similar to that of FIGS. 8 and 9 showing an alternative separation device employing a rotating drum having an outer peripheral screen.

Referring to FIG. 10, in yet another alternative embodiment, a drum 135 may be partially immersed approximately one-third to one-half in liquid held in container 141. The drum 135 has wire mesh 128 attached to its outer cylindrical periphery and may filled with cotyledons 12*d* and embryos 12*c* into solution and rotated as indicated by arrow 142, causing the embryos 12*c* to pass out of the drum 135, which retains the cotyledons 12*d*.

It is envisioned that other methods of embryo separation may also be used. For example, manual or automated sieving may be performed. Manual sieving may be performed using sieve trays immersed in liquid and gently shaking the trays.

Figure 11:
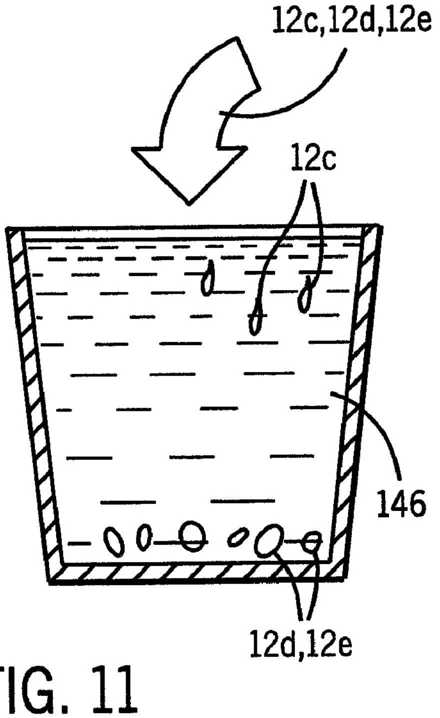
FIG. 11 is an elevational cross-section of a sucrose separation system in which a predetermined density of sucrose solution separates embryos from the remaining portions of the seed.

Referring to FIG. 11, in an alternative separation method, the cotyledons 12*d* and embryos 12*c* may be introduced into a sucrose solution 146 of predetermined density selected to cause flotation of the embryos 12*c* and the sinking of the cotyledons 12*d* and seed coats 12*e* which may then be separated by a skimming or pouring off the embryos 12*c*. The sucrose solution should be approximately 30-40% with thirty-seven percent preferred; however, concentrations of 10-70% will also provide some separation. After a few minutes, the embryos 12*c* rise to the surface of the container. The sucrose may be substituted with other biologically neutral compounds such as propylene glycol or Ficol, for example.

For each of these processes, the removed embryos may not be perfect, however, experimentation has shown that embryos with obscured meristems are still transformable. This separation need not be perfect as transformable tissue includes the embryo 12*c* with the primary leaves removed or with the primary leaves intact or with a partial cotyledon 12*d*.

Figure 12:
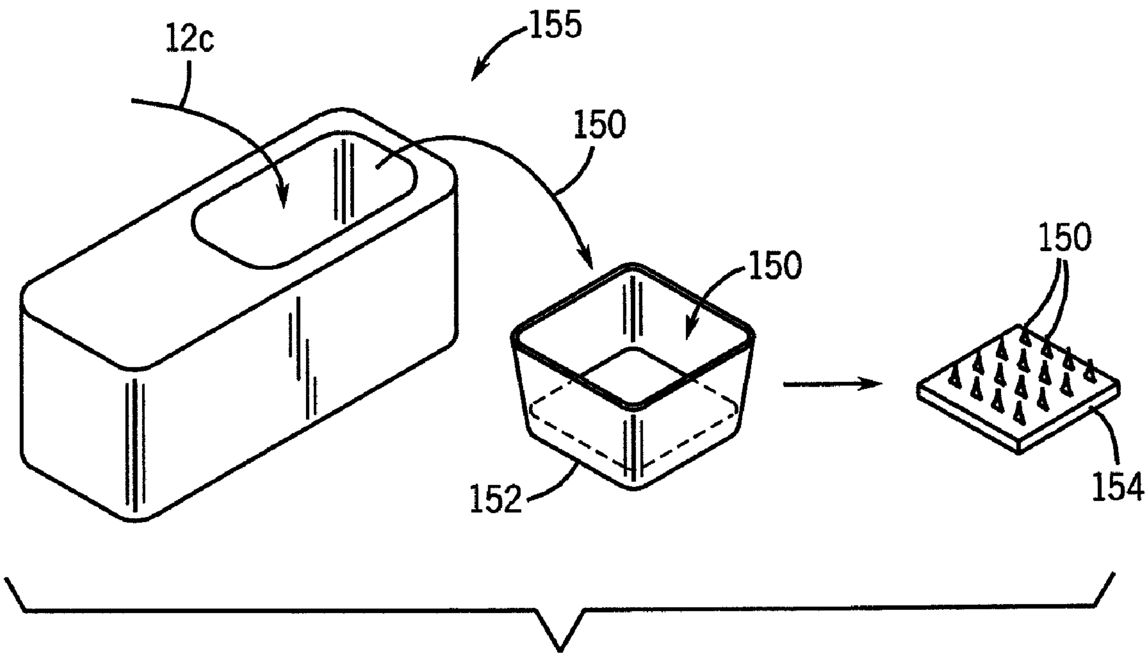
FIG. 12 is a flow diagram of an inoculation step in which the embryos are treated with *Agrobacterium* and processed in a viability test in a liquid media prior to culturing.

Referring now to FIGS. 1 and 12, once the embryos 12*c* are collected, they may be rinsed in sterile liquid or other solutions and then may be inoculated in a gene transfer step 155 with the desired genes using one of a variety of techniques, for example in soybean, sonication, as described in U.S. Pat. No. 6,384,301 issued May 7, 2002, assigned to the assignee of the present invention and hereby incorporated by reference, or particle delivery as described in U.S. Pat. No. 5,914,451 issued Sep. 22, 1992, assigned to the assignee of the present invention and also hereby incorporated by reference. Monocotyledonous plants could be transformed using the methods described in U.S. Pat. No. 5,591,616 issued Jan. 7, 1997, or PCT application WO95/06722 published Mar. 9, 1995, herein incorporated by reference. Cotton could be transformed using the methods described in U.S. Pat. No. 5,846,797 issued Dec. 8, 1998, or U.S. Pat. No. 5,004,863 issued Apr. 2, 1991 all hereby incorporated by reference.

Optionally, as indicated in process block 156 in FIG. 1, after sonication or other gene transfer step 155, the transplanted embryos 150 may be placed in a liquid culture 152 for fifteen to thirty days to identify which embryos 12*c* are still viable. This culturing also allows easier identification of the root and stem tips of the embryos 12*c* for proper planting of the viable embryos in an agar block 154 or further culture in liquid medium for selection. Up to this viability test, the amount of hand labor may be negligible and therefore nonviable embryos may still be removed at relatively low cost. Viability may also be tested on solid or semi-solid medium as well as liquid medium.

The proven viable embryos 12*c* are then grown on an agar block 154 such as may be treated with compounds or environmental conditions to help identify those embryos that have successfully received the implanted gene according to methods described in above-referenced U.S. Pat. No. 6,384,301.

The above-described techniques may be suitable for any plant whose transformable tissue can be derived from seeds and is especially useful for seeds of oilseed plants, such as soybean, canola, rapeseed, safflower, and sunflower, as well as other plants of commercial interest, such as legumes, cotton, corn, rice and wheat.

Generally each of the steps of FIG. 1 may be used independently of the others. It is specifically intended that the present invention not be limited to the embodiments and illustrations contained herein, but include modified forms of those embodiments including portions of the embodiments and combinations of elements of different embodiments as come within the scope of the following claims.

The invention claimed is:

1. An apparatus for bulk preparation of transformable plant tissue comprising:

(a) a hopper for receiving plant seeds;

(b) an excisor providing spaced apart moving surfaces applying a force to the seeds exiting from the hopper so as to divide the seeds into a separate cotyledon, seed coat and embryo, wherein the moving surfaces comprise rollers comprising one or more of: a serpentine roller face; an outer frictional surface; or an outer elastomeric surface; and (c) a separator separating the embryo from the seed coat and cotyledons.

2. The apparatus of claim 1 wherein the excisor provides moving surfaces applying a shear force to the seeds.

3. The apparatus of claim 1 wherein the rollers have different rolling speeds to provide a shear force.

4. The apparatus of claim 1 wherein the rollers are co-rotating.

5. The apparatus of claim 1 wherein the rollers have serpentine roller faces.

6. The apparatus of claim 1 wherein the rollers have an outer frictional surface.

7. The apparatus of claim 1 wherein rollers have an outer elastomeric surface.

8. The apparatus of claim 1 wherein the moving surfaces comprise at least two successive sets of opposed rollers.

9. The apparatus of claim 8 wherein the successive sets of rollers have decreasing separation as seeds progress through the successive sets of rollers.

10. The apparatus of claim 8 wherein the rollers have an outer elastomeric surface and wherein the outer elastomeric surfaces of successive sets of rollers have greater softness as seeds progress through the successive sets of rollers.

11. The apparatus of claim 1 including an adjustment means allowing adjustment of a separation of the moving surfaces according to a type of seed.

12. The apparatus of claim 1 including a motor speed control allowing adjustment of a shear between the moving surfaces according to a type of seed.

13. The apparatus of claim 1 including a spray head system adapted to spray the seeds with liquid as they pass through the moving surfaces.

14. The apparatus of claim 1 wherein the moving surfaces are rollers and including a spray head system having spray heads aimed to spray liquid against the rollers to strike the rollers in a direction opposite rotation of the rollers.

15. The apparatus of claim 1 including a seed conveyor providing a substantially predetermined constant volume rate of seed flow into the hopper.

16. The apparatus of claim 15 wherein the excisor is a pair of spaced apart rollers rotating about first axes and wherein the flow of seeds into the excisor on the seed conveyer is substantially perpendicular to the first axes.

17. The apparatus of claim 16 wherein the seed conveyor has a discharge pipe and further including a diverter bar centered in a path of the seeds from the discharge pipe to spread the seeds along an opening between the rollers.

18. An apparatus for bulk preparation of transformable plant tissue comprising:

(a) a seed hydrator comprising a container into which the seeds are held prior to being received by a hopper, the container having an outlet and an inlet, the inlet communicating with the first rinse liquid reservoir and a second soak liquid reservoir different from the rinse liquid reservoir and including valve means positioned between the inlet and the rinse liquid reservoir and the inlet and the soak liquid reservoir and the outlet and a drain, the valve means communicating with an electronic timer for automatically controlling a flow of liquids to the container from the first rinse liquid reservoir and the soak liquid reservoir and to the drain from the container;

(b) a hopper for receiving plant seeds from the seed hydrator;

(c) an excisor providing spaced apart moving surfaces applying a force to the seeds exiting from the hopper so as to divide the seeds into a separate cotyledon, seed coat and embryo; and (d) a separator separating the embryo from the seed coat and cotyledons.

19. The apparatus of claim 18 wherein the electronic timer operates to:

wet the seeds for a predetermined period of time after which excess liquid is drained away;

hold the seeds after wetting for at least one hour; and soak the seeds after the holding for at least 30 minutes.

20. The apparatus of claim 18 wherein the rinse liquid reservoir holds and antimicrobial.

21. The apparatus of claim 20 wherein the antimicrobial is bleach solution.

22. The apparatus of claim 18 wherein the soak liquid reservoir includes a germinating medium.

23. The apparatus of claim 1 including a source of liquid and wherein the separator separates the embryos and seed coats with a wash of liquid.

24. The apparatus of claim 23 wherein the liquid is water.

25. The apparatus of claim 23 wherein the separator includes a weir allowing the seed coats to wash over a top of the weir and the embryos and cotyledons to be passed to a bottom of the weir.

26. The apparatus of claim 1 wherein the separator provides a screen separating the cotyledons from the embryos.

* * * * *